United States Patent
Marchitto et al.

(10) Patent No.: US 11,612,427 B2
(45) Date of Patent: Mar. 28, 2023

(54) INDUCTIVE HEATING OF TISSUES USING ALTERNATING MAGNETIC FIELDS AND USES THEREOF

(71) Applicant: ROCKY MOUNTAIN BIOSYSTEMS, INC., Wheat Ridge, CO (US)

(72) Inventors: Kevin S. Marchitto, Golden, CO (US); Stephen T. Flock, Arvada, CO (US)

(*) Notice: Subject to any disclaimer, the term of this patent is extended or adjusted under 35 U.S.C. 154(b) by 272 days.

(21) Appl. No.: 16/600,677

(22) Filed: Oct. 14, 2019

(65) Prior Publication Data
US 2020/0155221 A1    May 21, 2020

Related U.S. Application Data

(63) Continuation of application No. 12/927,746, filed on Nov. 23, 2010, now Pat. No. 10,441,346, which is a
(Continued)

(51) Int. Cl.
*A61B 18/14* (2006.01)
*A61N 7/00* (2006.01)
(Continued)

(52) U.S. Cl.
CPC .............. *A61B 18/14* (2013.01); *A61N 2/002* (2013.01); *A61N 2/004* (2013.01); *A61N 2/02* (2013.01);
(Continued)

(58) Field of Classification Search
CPC ................................ A61B 2018/00023; A61B 2018/00452–00476; A61B 18/14; A61N 2/002; A61N 2/004; A61N 2/02
See application file for complete search history.

(56) References Cited

U.S. PATENT DOCUMENTS

| 4,889,120 A | 12/1989 | Gordon |
| 5,057,106 A | 10/1991 | Kasevich et al. |

(Continued)

OTHER PUBLICATIONS

"Electromagnetic radiation." Collins Dictionary of Astronomy. London: Collins, 2006. Credo Reference. Web. May 24, 2012.
(Continued)

*Primary Examiner* — Michael F Peffley
*Assistant Examiner* — Samantha M Good

(57) ABSTRACT

Provided herein are methods and devices for inductively heating a tissue to effect a biological response in the tissue or in a biomolecule comprising the same. The methods and devices comprise means for applying a high frequency alternating magnetic field via an inductive coil comprising an applicator to the tissue and means for monitoring feedback from the alternating magnetic field to control and/or adjust heat, for example, in the tissue, which further includes a means for cooling the tissue. Particularly, the device may be a hand held piece that incorporates or has at least an applicator, including a radiofrequency energy generator and output, an inductive coil, an impedance matching system, a cooling system, including a thermally conductive surface and a coolant housing containing a coolant that circulates through the thermally conductive surface, and a feedback monitor. Optionally, the device may comprise a tissue-shaper.

13 Claims, 10 Drawing Sheets

Related U.S. Application Data continuation-in-part of application No. 12/080,897, filed on Apr. 7, 2008, now Pat. No. 10,271,900.

(60) Provisional application No. 60/922,249, filed on Apr. 6, 2007.

(51) Int. Cl.
    *A61N 2/00* (2006.01)
    *A61N 2/02* (2006.01)
    *A61B 18/00* (2006.01)

(52) U.S. Cl.
    CPC ............ *A61B 2018/00023* (2013.01); *A61B 2018/0047* (2013.01); *A61B 2018/00452* (2013.01); *A61N 7/00* (2013.01)

(56) References Cited

U.S. PATENT DOCUMENTS

| | | | |
|---|---|---|---|
| 5,366,443 A | 11/1994 | Eggers et al. | |
| 5,412,182 A | 5/1995 | Chan | |
| 5,429,583 A | 7/1995 | Paulus et al. | |
| 5,824,015 A | 10/1998 | Sawyer | |
| 5,897,495 A | 4/1999 | Aida et al. | |
| 6,074,385 A | 6/2000 | Klopotek | |
| 6,148,236 A | 11/2000 | Dann | |
| 6,171,321 B1 | 1/2001 | Gifford et al. | |
| 6,208,903 B1 | 3/2001 | Richards et al. | |
| 6,241,753 B1 | 6/2001 | Knowlton | |
| 6,350,274 B1 | 2/2002 | Li | |
| 6,451,044 B1 | 9/2002 | Naghavi et al. | |
| 6,458,109 B1 | 10/2002 | Henley et al. | |
| 6,656,174 B1 | 12/2003 | Hegde et al. | |
| 6,814,712 B1 | 11/2004 | Edwards et al. | |
| 7,189,230 B2 | 3/2007 | Knowlton | |
| 7,463,251 B2 | 12/2008 | Giraldo et al. | |
| 7,967,839 B2 | 6/2011 | Flock et al. | |
| 10,271,900 B2 | 4/2019 | Marchitto et al. | |
| 10,441,346 B2 | 10/2019 | Marchitto et al. | |
| 2003/0032950 A1 | 2/2003 | Altshuler et al. | |
| 2004/0122494 A1 | 6/2004 | Eggers et al. | |
| 2004/0127895 A1 | 7/2004 | Flock et al. | |
| 2004/0210214 A1 | 10/2004 | Knowlton | |
| 2005/0182462 A1* | 8/2005 | Chornenky | A61N 1/0424 607/99 |
| 2008/0249350 A1 | 10/2008 | Marchitto et al. | |
| 2011/0077451 A1 | 3/2011 | Marchitto et al. | |
| 2016/0038753 A1 | 2/2016 | Chornenky et al. | |
| 2016/0317827 A1 | 11/2016 | Schwarz et al. | |
| 2016/0346561 A1 | 12/2016 | Ron Edoute et al. | |
| 2019/0183562 A1 | 6/2019 | Widgerow | |

OTHER PUBLICATIONS

Anderson, "Fire and ice," Arch Dermatol., 139(6):787-788, Jun. 2003.

Cameron, editor. "Diathermy," Physical Agents in Rehabilitation, 4th Edition, Chapter 10, pp. 202-222, published 2012, originally published 1999.

Cameron, editor. "Pain," Physical Agents in Rehabilitation, 4th Edition, Chapter 4, pp. 46-71, published 2012, originally published 1999.

Cameron, editor. "Physical Agents in Clinical Practice," Physical Agents in Rehabilitation, 4th Edition, Chapter 2, pp. 15-22, published 2012, originally published 1999.

Cameron, editor. "Superficial Cold and Heat," Physical Agents in Rehabilitation, 4th Edition, Chapter 8, pp. 129-172, published 2012, originally published 1999.

Cameron, editor. "The Physiology of Physical Agents," Physical Agents in Rehabilitation, 4th Edition, Chapter 1, pp. 1-14, published 2012, originally published 1999.

Cameron, editor. "Tone Abnormalities," Physical Agents in Rehabilitation, 4th Edition, Chapter 5, pp. 72-105, published 2012, originally published 1999.

Franco et al., "Hyperthermic injury to adipocyte cells by selective heating of subcutaneous fat with a novel radiofrequency device: feasibility studies," Lasers Surg Med., 42(5):361-370, Jul. 2010.

Klein, "Deep Heat," emedicine.medscape.com [online] dated Sep. 25, 2008. Retrieved from the Internet <URL: http://emedicine.medscape.com/article/325046-print>, retrieved on Jan. 27, 2010, 8 pages.

Leitgeb, "Exposure of non-target tissues in medical diathermy," Bioelectromagnetics, 31(1):12-19, Jan. 2010.

\* cited by examiner

Untreated

Treated + 2 weeks

Treated + 2 weeks

Untreated control

Treated

INDUCTIVE HEATING OF TISSUES USING ALTERNATING MAGNETIC FIELDS AND USES THEREOF

CROSS-REFERENCE TO RELATED APPLICATIONS

This application is a continuation of U.S. patent application Ser. No. 12/927,746 filed Nov. 23, 2010, now U.S. Pat. No. 10,441,346, which is a continuation-in-part of U.S. patent application Ser. No. 12/080,897 filed Apr. 7, 2008, now U.S. Pat. No. 10,271,900, which issued on Apr. 30, 2019, which claims the benefit of U.S. Provisional Application No. 60/922,249, filed Apr. 6, 2007, the entirety of which are hereby incorporated by reference.

BACKGROUND OF THE INVENTION

Field of the Invention

The present invention relates generally to the fields of biomedical engineering, biochemistry, medical treatment, and surgical procedures. More specifically, the present invention provides methods, devices, and compositions for inducing changes in tissues, biomolecules, including bioactive molecules. These changes are notably useful for inducing alterations in tissues, most notably in skin, for cosmetic purposes.

Description of the Related Art

Heating of tissue is a fundamental physical event in many different medical procedures. Depending on the time-temperature history of the tissue, a cascade of physical, chemical, and biological events occurs when tissue is heated. These events can lead to a beneficial or deleterious response. One example of a beneficial response is the reduction or elimination of the appearance of skin wrinkles as a result of heat induced tissue contraction and skin thickening as a result of neocollagen formation following heat stimulation in tissues.

Skin wrinkles are often the consequence of advancing age and sun exposure. With increasing age and excessive sun exposure, skin quality deteriorates. This is due, in part, to changes in hydration and epidermal thickness, and on a molecular scale, to a decrease in the amount of collagen in the dermis. Further, subcutaneous fat accumulates or atrophies leading to furrowing of the skin, which produces wrinkles. In today's society, the appearance of skin wrinkles is often viewed negatively and so there is a desire in the community for a means to safely reduce or eliminate wrinkles.

For many years, wrinkles have been treated with chemical peels or mechanical dermabrasion, cosmetic medical procedures in which the surface of the epidermis of the skin, i.e., the stratum corneum, is removed chemically or by abrasion, such as sanding, respectively. In the late 1980s, laser ablation procedures for skin resurfacing were developed and approved.

Some of the first laser ablation procedures involved $CO_2$ lasers, which ablated some or all of the outermost layer of the epidermis, the stratum corneum. The $CO_2$ lasers could often generate enough heat in the dermis to cause a tissue contraction. This and subsequent repair of the epidermis and stratum corneum led to visible effects including wrinkle reduction and smoothing of the skin.

Nonetheless, inadvertent and lasting damage from burns to the epidermis was often evident, hypo- or hyper-pigmentation was fairly common, and patients receiving these treatments were required to stay indoors for weeks in order to avoid damaging ultraviolet rays from sunlight in their now unprotected dermal layers of skin. These lasers gave way to various lasers that operated at different wavelengths with the goal of reducing the negative effects. Today, laser procedures that are non-ablative and less damaging to surrounding tissues have replaced most of these original laser procedures. These lasers are much safer and produce much less damage to surrounding tissues, however much of the beneficial effects have also been lost, particularly with regard to skin tightening.

In the mid to late 1990s, another cosmetic technique for skin was developed that involves a non-ablative thermal alteration to skin. This procedure was based on concepts drawn from radiofrequency electrosurgical devices where electrical current is introduced into the patient via an electrode in electrical contact with tissue and exits through a ground electrode in contact elsewhere on the patient. These devices are referred as capacitive coupled devices whereby current flows between electrodes, and on the way, fields build up where tissues of relatively greater resistance are encountered.

In the case of skin, the stratum corneum and epidermis are only weakly conductive, so fields and heat build up there. Current flows through the conductive dermis, and again encounters resistance at the adiposal level, again resulting in heat generation. In skin, the treatment technique is referred to as radiofrequency (RF) skin rejuvenation (1).

In the skin, beneficial radiofrequency rejuvenation can result in tissue contraction as heat flows from the areas of field concentration, such as the adipose layer and epidermis, and into the dermis. Furthermore, a beneficial wound response to the heat in the dermis can lead to production of new collagen, and ultimately the skin may thicken. When treating the skin with RF devices, it is necessary to provide a conductive coupling gel between the skin and electrodes to allow for current flow.

Capacitive-coupled devices may result in negative, and sometimes severe consequences with regard to damage to tissues where the electric fields concentrate. Current generally follows the path of least resistance and thus it is not always predictable or controllable where its effects will occur. Any current that flows through the body is potentially hazardous. As the electric fields concentrate at non-conductive interfaces, electrical burns and heat damage may become evident at these interfaces. Burns are common at the electrodes in electrosurgical devices, and similarly, RF rejuvenation devices may also produce burns. In skin, capacitively-coupled radiofrequency heating exhibits preferential power absorption in the epidermis and in lower-conductivity subcutaneous fat. In other words, capacitive-coupled devices preferentially heat tissues with higher specific resistance (2-3). As a result, these tissues are at risk for damage.

To counter the effects of deleterious heating at the skin surface, capacitive-coupled skin rejuvenation devices (4), and lasers (5-6), often use some mechanism to cool the surface of the skin, thereby avoiding most of the damage to the outer epidermis and stratum corneum. Nonetheless, the risk of heating adipose tissue below the dermis is ever present with RF devices and, anecdotally, patients have complained of long-term subcutaneous fat atrophy following treatment with these devices, with some of these requiring grafting. Efforts to reduce such detrimental effects require reduction of power output and have likely reduced efficacy of these devices.

More recently, additional devices for skin rejuvenation have been developed that employ ultrasound In an attempt to provide specific and localized treatment to the dermis. The devices focus the ultrasound within the dermis, or just below to achieve specific heating. Though specificity is improved, cavitation can result in pain and tissue damage. Burning and necrosis of the epidermis and stratum corneum during laser and RF cosmetic skin treatments is of major concern. Thus, various methods of skin cooling are often employed, including the spraying of cryogen on the skin surface or on an applicator, or applying cold air, water or ice to the skin.

In contrast to the aforementioned tissue heating devices and technology, magnetic induction applicators, such as those used in magnetic induction diathermy devices primarily induce (eddy) currents to flow along pathways governed by electric conductivities, hence depositing more power in tissues of higher conductivity (2). Inductively coupled diathermy units use induced eddy currents to heat tissue, especially tissue, such as muscle, with high water content (7), but only weakly affect tissues with high fat content (8). Nonetheless, diathermy devices are used for deep heating of tissue structures, and their effects on thin tissue layers such as the dermis have yet to be described.

Thus, there is a recognized, continuing need for improved methods and devices for specific heating of the thin dermal layer of skin with a high degree of specificity, efficacy and safety. Moreover, there is a recognized need for improvements in the use of magnetic induction methods and devices to heat tissue near or at the skin surface, and particularly, for specific dermal heating to achieve a cosmetic result.

The prior art is deficient in methods and devices for highly efficient and safe non-invasive heating of the skin, with high specificity for the dermis, while protecting collateral tissue structures. The present invention fulfills this longstanding need and desire in the art.

SUMMARY OF THE INVENTION

The present invention is directed to a method for inducing heat in the dermis of a subject to effect a biological response. The method comprises the step of applying a high frequency alternating magnetic field to the skin of the individual such that the magnetic field inductively heats the dermis, thereby effecting the biological response therein. In a related method an area of skin is mechanically or pneumatically shaped prior to applying the high frequency alternating magnetic field thereto. In another related method, one of radiant energy, acoustic energy or vibrational energy is applied to the skin concurrently or sequentially with the high frequency alternating magnetic field. In yet another related method, feedback from the magnetic field is monitored and an amount of heat induced in the dermis in the individual is adjusted based on the feedback. In yet another related method, the dermis of the subject is cooled to disperse heat generated therein.

The present invention also is directed to a device for heating a tissue in a subject. The device comprises a means for generating a high frequency alternating magnetic field to alter one or both of a tissue or a biomolecule comprising the same in the subject and a means for controlling the alteration of the tissue or biomolecule. A related device further incorporates a means for housing the device. Another related device further incorporates a means for monitoring feedback from one or more of another source of radiant energy, plasma energy, acoustic energy, or bipolar or monopolar electrosurgical energy.

The present invention is directed further to another device for heating tissue in a subject. The device comprises a hand held piece that incorporates or has an applicator with a radiofrequency energy generator and an energy output, an impedance matching network in electrical contact with the applicator, an inductive coil connected to the energy output, an end plate at a distal end of the hand held piece that has a thermally conductive surface positionable on the tissue and, optionally, is in thermal contact with the inductive coil. A related device further comprises a coolant housing containing a coolant and in fluid contact with the inductive coil and, optionally, the thermally conductive surface. Another related device further comprises a mechanical tissue-shaper or a pneumatic tissue-shaper in contact with the tissue. Another related device further comprises a heat feedback monitor positioned distal to the induction coil or proximate to the tissue.

Other and further aspects, features, and advantages of the present invention will be apparent from the following description of the presently preferred embodiments of the invention given for the purpose of disclosure.

BRIEF DESCRIPTION OF THE DRAWINGS

So that the matter in which the above-recited features, advantages and objects of the invention, as well as others that will become clear, are attained and can be understood in detail, more particular descriptions of the invention briefly summarized above may be had by reference to certain embodiments thereof that are illustrated in the appended drawings. These drawings form a part of the specification. It is to be noted, however, that the appended drawings illustrate preferred embodiments of the invention and therefore are not to be considered limiting in their scope.

DETAILED DESCRIPTION OF THE INVENTION

Figure 1:
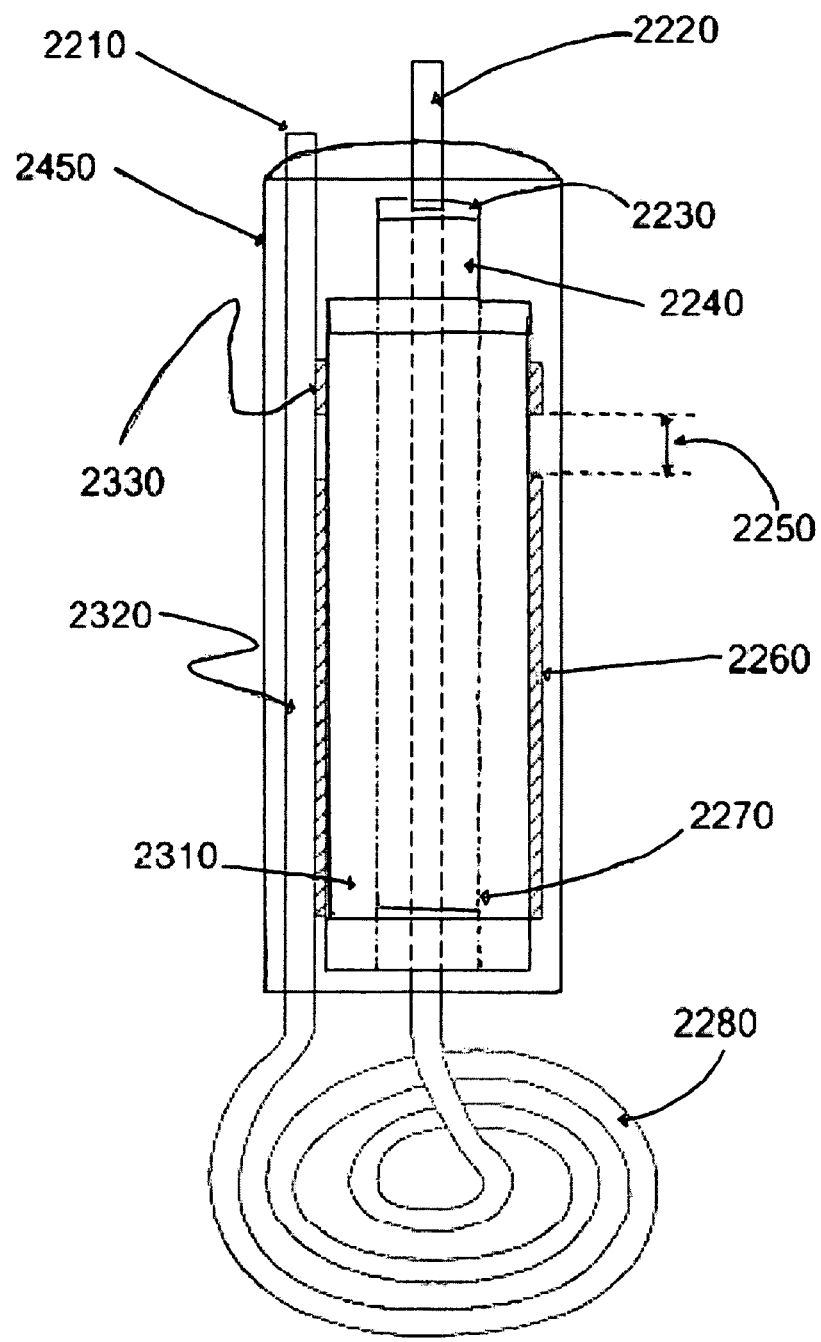
FIG. 1 depicts an applicator that transduces radiofrequency electrical energy into a magnetic field.

As used herein, the term, "a" or "an" may mean one or more. As used herein in the claim(s), when used in conjunction with the word "comprising", the words "a" or "an" may mean one or more than one. As used herein "another" or "other" may mean at least a second or more of the same or different claim element or components thereof.

As used herein, the term "or" in the claims refers to "and/or" unless explicitly indicated to refer to alternatives only or the alternatives are mutually exclusive, although the disclosure supports a definition that refers to only alternatives and "and/or".

As used herein, the term "subject" refers to any recipient of at least high frequency alternating magnetic field as a means for inductively heating a tissue, for example, the skin or dermis, thereof to cause or to effect a biological response in the tissue or its components or biomolecules comprising the same.

In one embodiment of the present invention there is provided a method for inducing heat in the dermis of a subject to effect a biological response, comprising the step of applying a high frequency alternating magnetic field to the skin of the individual, whereby the magnetic field inductively heats the dermis, thereby effecting the biological response therein.

Further to this embodiment the method may comprise mechanically or pneumatically shaping an area of skin prior to applying the high frequency alternating magnetic field thereto. In another further embodiment the method may comprise applying radiant energy, acoustic energy or vibrational energy to the skin concurrently or sequentially with the high frequency alternating magnetic field.

In another further embodiment the method may comprise monitoring feedback from the magnetic field and adjusting an amount of the heat induced in the dermis in the individual based on the feedback. In this further embodiment the step of feedback monitoring may comprise one or more of detecting heat in the dermis, detecting eddy currents formed in the dermis, detecting hydration changes in the dermis, or detecting impedance changes in the dermis. In representative examples detecting heat in the dermis may comprise monitoring heat sensitive liquid crystal media or monitoring infrared radiation. Further to this embodiment feedback monitoring further may comprise monitoring heat generated by one or more of another source of radiant energy, plasma energy, acoustic energy, or bipolar or monopolar electrosurgical energy.

In yet another further embodiment the method may comprise cooling the dermis of the subject to disperse heat generated therein. In this further embodiment the step of cooling the dermis may comprise positioning a thermally conductive surface in contact with one or both of the skin or an exterior surface of an inductive coil generating the alternating magnetic field. A thermally conductive surface may be a heat sink that passively disperses heat, may have a coolant circulating therethrough, may be a cryogenic material or may have a cryogenic material disposed thereon.

In all embodiments the biological response may be one or more of tissue coagulation, cauterization, tissue contraction, tissue shrinkage, induction of wound response, production of collagen. Also, the inductive heating may activate collagen repair and tissue growth or improves skin cosmesis by smoothing the skin or reducing skin laxity.

In another embodiment of the present invention there is provided a device heating a tissue in a subject, comprising means for generating a high frequency alternating magnetic field to alter one or both of a tissue or a biomolecule comprising the same in the subject; and means for controlling the alteration of the tissue or biomolecule.

In this embodiment the means for providing the high frequency alternating magnetic field may be an applicator having an induction coil and an output for radiofrequency energy. Also in this embodiment the means for controlling the alteration of the tissue or biomolecule may comprise a monitoring system for feedback from the high frequency alternating magnetic field distal to the induction coil or proximate to the tissue.

Further to these embodiments the device may comprise means for housing the device. In this further embodiment the means for housing the device may be a hand held piece having an impedance matching network and a coupler to couple to an output of a radiofrequency energy source. Also, in this further embodiment the hand held piece further may comprise an end plate at a distal end thereof and having a thermally conductive surface positionable to contact one or both of the tissue or the exterior of the applicator. Examples of a thermally conductive surface are a passive heat sink, a cryogenic material or the thermally conductive surface has a cryogenic material applied thereto. In addition, the hand held piece further may comprise a coolant housing attached thereto and containing coolant which is in fluid contact with one or both of the thermally conductive surface on the end plate and an inductive coil comprising an applicator where the coolant circulates therethrough. Furthermore, the hand held piece further may comprise a mechanical tissue-shaper or a pneumatic tissue-shaper in contact with the tissue.

In another further embodiment the device may comprise means for monitoring feedback from one or more of another source of radiant energy, plasma energy, acoustic energy, or bipolar or monopolar electrosurgical energy. In all embodiments the tissue may be skin.

In yet another embodiment of the present invention there is provided a device for heating a tissue in a subject, comprising a hand held piece incorporating an applicator with a radiofrequency energy generator and an energy output; an impedance matching network in electrical contact with the applicator; an inductive coil connected to the energy output; and an end plate at a distal end of the hand held piece that has a thermally conductive surface positionable on the tissue and, optionally, is in thermal contact with the inductive coil.

In a further embodiment the device may comprise a coolant housing containing a coolant and in fluid contact with the inductive coil and, optionally, the thermally conductive surface In another further embodiment the device may comprise a mechanical tissue-shaper or a pneumatic tissue-shaper in contact with the tissue. In yet another further embodiment the device may comprise a heat feedback monitor positioned distal to the induction coil or proximate to the tissue. In all embodiments the tissue may be as described supra.

The present invention provides methods and devices for treatment of tissues in a subject, preferably for cosmetic treatment of skin, with a high degree of specificity for the dermis. The devices are magnetic induction devices of such geometry that they provide a concentrated and intense alternating magnetic field to shallow layers of skin, when placed in close proximity to the skin. The method involves creating a high-frequency alternating magnetic field that, when directed in proximity with tissue, results in the production of heat through inductive coupling with the tissue thus resulting in the desired biologic effect. Representative examples of such biologic effects include, but are not limited to coagulation, cauterization, tissue contraction or shrinkage, and induction of a wound response that leads to biomolecular changes. Generally, application of the high frequency alternating magnetic field itself may induce, or the concomitant production of heat may induce, the movement of a charged species or other biomolecule or bioactive molecule or species within the tissue leading to various biological responses, such as, but not limited to, the production of collagen by cells and dermal thickening.

Particularly, utilizing the present methods and devices improves the cosmetic appearance of the skin by controllably heating a superficial layer of skin, preferably, the dermis. An acute tissue contraction or shrinkage and/or a wound response is effected which leads to the production of biomolecules resulting in improved cosmesis. Preferably, the devices are used for the direct heating of moist conductive tissues, such as the viable dermis, during cosmetic skin treatment, and less efficiently for tissues of low conductivity which may in part be due to low hydration (e.g. stratum corneum) or of low polarity (adipose), thereby providing a safer means for treating skin. The device and its method of use minimizes the risk of significant burns to the skin surface, and eliminates charring and the generation of smoke, as it does not rely on capacitive coupling for its effects. The patient is isolated from the electrical current in the devices and no electrical current is conducted from the applicator or the patient.

Generally, the devices provided herein comprise a means for generating and applying a high frequency alternating magnetic field, a means for controlling the alteration of the tissue or biomolecule contained therein, a means for monitoring feedback related to heat generation, and a means for housing the device. Particularly, the devices may be hand held such that a hand held piece incorporates a source of radiofrequency electrical energy coupled to a coil and an impedance matching network to produce an alternating magnetic field. When tissue is brought into proximity of the alternating magnetic field, heating of the tissue results as a consequence of either or both of dipole formation and oscillation or eddy current formation.

Optionally, cooling is provided to remove or disperse heat from the coil, the source of RF electrical energy, or the surface of the skin alone or in combination. For example, a disposable or permanent tip, or cover placed between the induction coil and the skin provides a thermally conductive surface that absorbs and distributes heat arising from the skin surface, for example, as a heat sink. Alternatively, a thermally conductive substance may be placed on the skin or tissue. Also, feedback monitoring of heat generation, eddy current formation in the tissue, ultrasound detection of tissue alterations, changes in impedance in tissues that lead to an impedance mismatch between the magnetic field applicator and the radiofrequency generator, hydration, etc. provides for the adjustable control of inductively generated heat in the tissue and/or device The methods and devices provided herein exhibit the significant benefits of, among other things, being non-invasive, not requiring electrical contact with the body of the subject, and providing controllable heating only to a thin layer of tissue. The invention is useful not only for cosmetic procedures such as facial rejuvenation, wrinkle treatment, acne treatment, hair removal, vascular lesion treatment, varicose vein treatment, curing of fillers, and treatment of cellulite, but also for surgical procedures such as coagulation, cauterization or for induction of biomolecular events, such as, but not limited to, a wound response, production of heat-shock proteins or an inflammatory response in tissue.

As described below, the invention provides a number of therapeutic advantages and uses, but such advantages and uses are not limited by such description. Embodiments of the present invention are better illustrated with reference to the Figures, however, such reference is not meant to limit the present invention in any fashion. The embodiments and variations described in detail herein are to be interpreted by the appended claims and equivalents thereof.

Radiofrequency Power Supply

The invention consists of a source of radiofrequency (RF) electrical energy, which may be supplied using a RF generator such as sold by Comdel, Inc. (e.g. CV1000 or CV500, preferably 40.68 MHz or 27.1 MHz; Gloucester, Mass.). The electrical output of the generator is coupled to an applicator consisting of an inductor in the form of a coil (for the generation of a magnetic field), which is further part of an impedance matching network that may additionally comprise a capacitor. The source of energy used may be a constant current or a constant voltage power supply or may be a modulated current or a modulated voltage power supply.

The power-supply is able to produce radiofrequency energy with a power in the range 10-10,000 W and, depending on the application, preferably in the range of about 100 to about 1000 W. The power-supply may typically operate at frequencies of about 100 kHz to about 5.8 GHz. Preferably the frequency range is about 1 MHz kHz to about 5.8 GHz and, more preferably, the frequency range is at or near, or between 13.56 MHz, 27.12 MHz, 40.68, 67.8 MHz, 95 MHz, 433.92, 915 MHz, 2.4 GHz. Beneficially, the RF generator may be frequency-agile; that is, as the impedance of the load changes somewhat, the frequency output of the RF generator changes slightly to provide a better impedance match between the load and the generator and so to maintain the output power within a controllable tolerance.

Applicator

FIG. 1 is a sectional view of an applicator used to produce a magnetic field. A center copper tube 2220, which serves to conduct the RF electricity but also serves as an input for refrigerant, is surrounded by a teflon cylinder 2240. Endcaps 2230 and 2270 server to position and hold the copper tube within the teflon cylinder. The center copper tube 2220 is formed at the distal end of the applicator into a coil, 2280, which then is fixed parallel 2320 with the center copper tube and directed to an exit 2210 out of the applicator; the coolant is directed out through exit 2210.

In order to provide impedance matching between the RF generator and applicator, a ceramic insulator 2310 is positioned around the teflon cylinder 2240. The ceramic insulator has two capacitor rings, 2330 and 2260, made up of copper pipe. The pipe 2320 is in electrical contact with the capacitor rings. By adjusting the spacing 2250 between the two capacitor rings, the impedance match between the RF generator and applicator can be effected. The applicator is encased in a copper cylinder 2450 attached to the ground shield of the coaxial wire in order to shield any stray radiated RF.

Handpiece

Figures 2A, 2B:
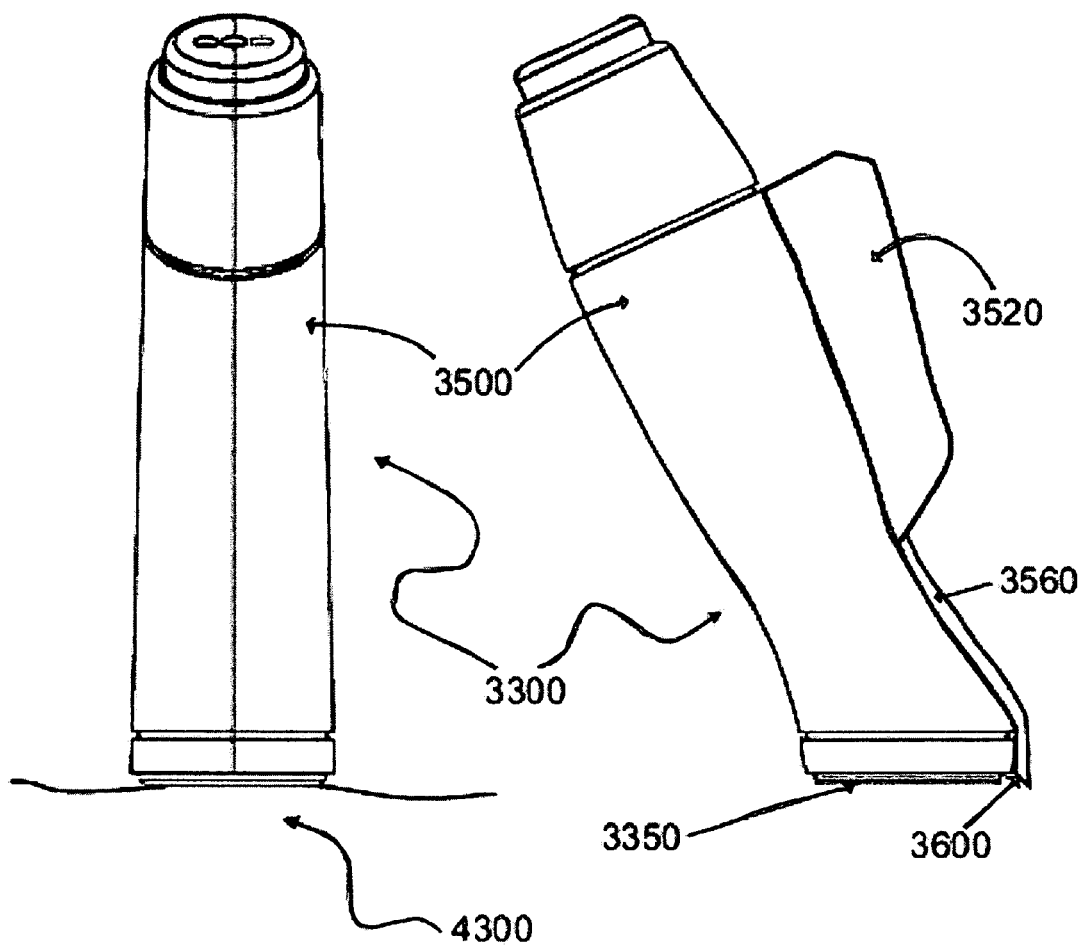
FIGS. 2A-2B depict a front view (FIG. 2A) and a side view (FIG. 2B) of a hand piece incorporating a magnetic field applicator with optional cooling system.

FIGS. 2A-2B show front and side views of one design for a hand piece 3300, which is made of an electrically non-conductive material such as plastic, which surrounds or encases the applicator. A first main housing 3500 is attached to a shield, or tip 3350, which is optionally disposable, which may be thermally conductive, which serves to maintain cleanliness of the part of the handpiece which comes into contact with the skin 4300, and which may serve to disperse or distribute heat. Optionally, the hand piece incorporates a coolant, for example, R-134a, contained in a second coolant housing 3520 and directed through a solenoid and pipe 3560 to an exit nozzle 3600. This coolant can be controllably directed to the treated tissue before, during and/or after the treatment in order to limit the heating of the very superficial skin.

Cooling Endplate

Figure 3:
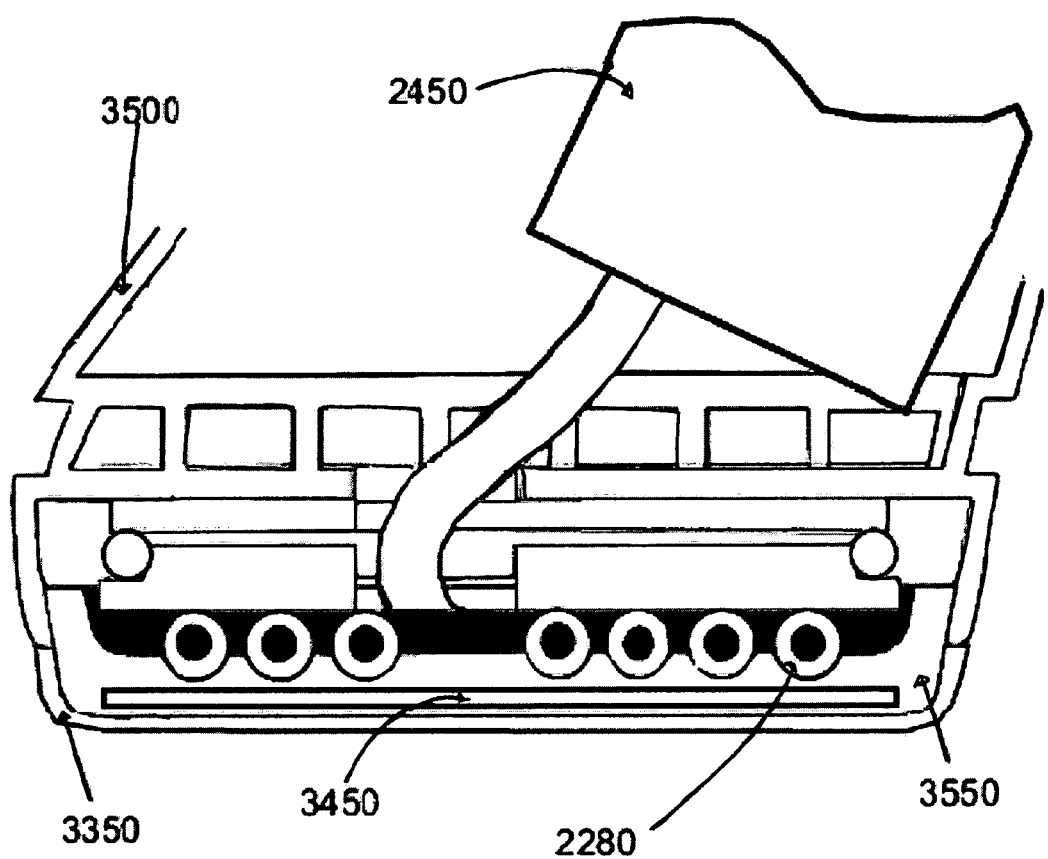
FIG. 3 depicts the endplate of the hand piece.

FIG. 3 shows a view of an endplate 3550, on the distal end of the hand piece housing 3500. The endplate is in intimate thermal contact with the coil 2280, which has circulating refrigerant or coolant within, and so the endplate is cooled. This coolant may optionally be supplied from a circulating chiller utilizing water and antifreeze. Alternatively, gas such as air, nitrogen, freon, R-12, R-134a, and carbon dioxide could serve the purpose of cooling. An optional, removable shield or tip 3350 may be in intimate contact with the endplate, thereby providing a means for the coolant to maintain an ambient temperature in the shield or tip.

FIG. 3 also shows an optional Faraday shield 3450, which is a conductive element intended to reduce capacitive coupling of coil to the subject and so to minimize any stray electric field. Note that the cooling endplate may be in intimate contact with the coil in order to provide optimal thermal conduction. This may be accomplished by molding or by forming the plate around the coil.

Pneumatic Applicator

Figure 4:
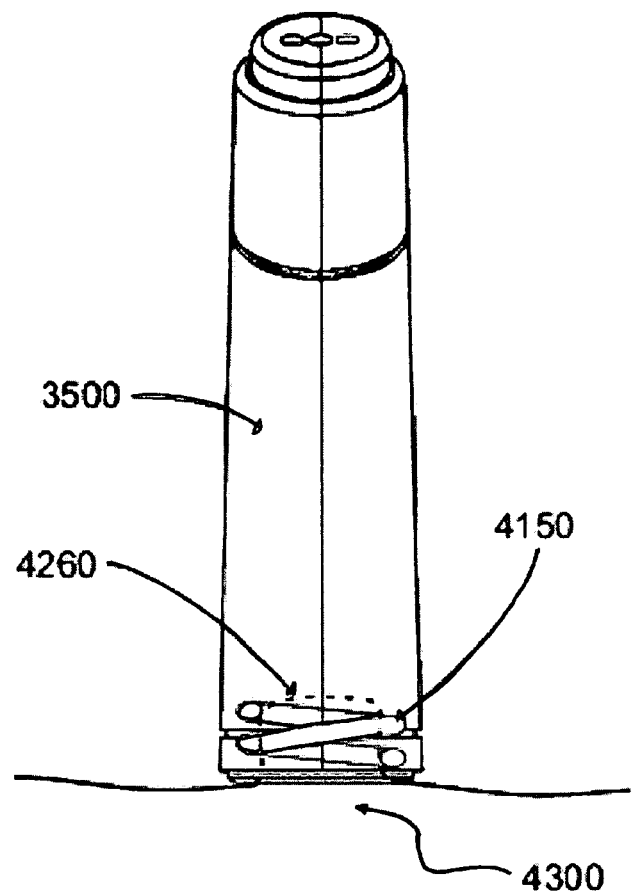
FIG. 4 depicts a hand piece incorporating a solenoid-type inductor and positioning of tissue using pneumatic pressure.

FIG. 4 shows a partial view of an applicator incorporating a two-turn solenoid coil 4150, the bore of which surround tissue 4260 which extrudes from the skin 4300 up into the bore as a result of negative pneumatic pressure within the housing 3500. As the magnetic field within the turns of a solenoid is very much stronger than the field outside of a pancake coil, and the geometry of the tissue within the bore is different than illustrated in FIG. 2A, the power required to obtain an effect is reduced and the effect on tissue can be more beneficial. Alternatively, a mechanical tissue-shaper may be positioned in contact with the skin.

Combined Devices

In some aspects of this embodiment, the treatment may be inductively, or conductively or radiatively applied in combination with the use of an alternating magnetic field. Additionally, the energy may be pulsed in order to improve the thermal kinetics of the tissue heating. Examples of applied energy are radiofrequency energy, radiant energy or vibrational energy. The radiofrequency energy may have a frequency from about 20 kHz to about 40 GHz, and may be applied using coils, electrodes or one or more antennae. The radiant energy may have a wavelength from about 600 nm to 11 µm. The vibrational energy may be sonic or ultrasonic with a frequency from about 20 Hz to 80 MHz. In the case of inductive heating, the energy may not be incident on the target, but may be induced in the target to be converted from one form to another.

In certain aspects, combined devices, using induction plus an energy source, e.g. laser or ultrasound, may enhance the effects or be used to combine certain treatments. Because the interaction of laser energy and ultrasound waves with tissue is physically different than the present invention, synergistic and combination effects are possible. For example, it may be desirable to treat the stratum corneum and epidermis with an alternate form of energy simultaneously, or sequentially, while treating with magnetic induction, thereby resulting in greater volumetric treatment of the skin. An applicator of radiant energy may comprise an optical assembly which focuses the radiant energy on the relevant target or below the target surface to get a sub-surface effect sparing the superior surface. A pressure-wave applicator may consist of a focused ultrasound transducer, which is coupled to the target tissue with an acoustic impedance matching material, such as gelatin, mineral oil or glycerin.

Feedback Monitoring and Safety Interlocks

In its preferred embodiment (FIGS. 1, 2A-2B), the device includes a means of monitoring the progress of the effect in tissue. For example, the alternating magnetic field results in tissue heating, this in turn alters the electrical properties of the target tissue. The tissue heating may have effects that alter electrical properties of the tissue either transiently or permanently. The effects could include dehydration, coagulation and rearrangement of molecules for example. These changes may be detected as a change in impedance, or by monitoring hydration or eddy current formation. For example, as the impedance of the skin changes, the impedance match between the RF generator and the tissue/applicator is generally altered, and this change may be detected through changes in power absorption, or changes in frequency. This change can alternatively be used as a signal to determine the level or duration of application of energy. Alternatively, the change in tissue can be detected using ultrasound to detect morphological changes. Change in the flow of eddy currents may be detected as being an indicator of the progress of reaction, and may reflect morphological changes, dehydration or heat in the system.

As the tissue treatment process is initiated, the applicator (FIG. 1) and, most notably, the coil 2280, endplate (FIG. 3, 3550), and tissue may increase in temperature. When the RF energy ceases, the temperature will fall. Such temperature changes can be monitored by devices such as thermocouples or thermistors. At times such devices can behave erratically in the presence of strong electromagnetic fields. Therefore, devices such as infrared thermometers may be more suitable to monitor the temperatures. These may be placed distal to the source of radiation, if required, and the signals transmitted through fiber optics.

Another approach to monitoring heat at the site of treatment involves monitoring temperature sensitive chemicals placed at the treatment site. These heat sensitive chemicals may be in the form of liquid crystals disposed on a film and placed in contact with the treatment site. The liquid crystals may change color upon reaching certain temperature thresholds, and may be monitored by collecting and detecting reflected light.

Transducers monitoring the temperature and power output of the RF generator, the reflected power into the generator, the presence of water flow into the applicator and, if it is required, the generator, where the presence of a short-circuit anywhere, which are indicated by a rapid rise in current in the generator and/or applicator, are an important safety feature in the present invention. Other optional safety interlocks include mechanical or electrical transducers between the disposable shield (FIG. 3, 3350) and the housing of the hand piece; if a shield is not present, the RF generator would not engage. Encoding of the interlock in the shield would ensure that a particular shield is only used on a particular patient. Thermal switches are incorporated within the device to shut it down if overheating occurs. Fast breakers quickly cut off the output if a power-output transient occurs. Multiple interlocks are incorporated within the device, which prevents running the device with the cover removed. A foot pedal optionally is incorporated in order to minimize the possibility of unintentional activation of the device.

The induced magnetic field also may be actuated or amplified upon detection of a load. A relatively small current may be applied to the device while the device is not in proximity to a tissue target. As the device becomes proximal to the target, the change in impedance is detectable, and this may be used as a signal to increase power to the device. In this example, the hand piece in place on the skin is matched as a unit, i.e. skin and hand piece, to achieve the impedance match with the power supply. Where there is a mismatch, the power will not be delivered. This safety feature minimizes the exposure of the hand piece components to significant power load when the device is not applied to tissue, thus potentially reducing wear of the device, as well as protecting the patient and operator.

Methods of Treatment

The device may be used to induce changes in tissue by applying alternating magnetic fields to the tissue such that currents are induced within the tissue (eddy currents). These currents encounter resistance and the result is the generation of heat. These eddy currents form most efficiently where there is a moist, polar environment, thus enabling electron displacement or ion flow within the target. Thus, for example, in skin, the generation of eddy currents in the moist underlying dermis is favored over the superficial dehydrated epidermis and stratum corneum layers, and the underlying, more non-polar adipose layer. This differential in conductivity results in preferable heating of conductive (dermis) tissues over non- or weakly-conductive tissues.

Sufficient induced energy is required to generate enough heat to overcome the effects of cooling from the body and blood flow. Therefore, the coil is preferentially configured so as to place the magnetic field in close proximity to the skin surface and deliver a high frequency, intense alternating magnetic field such that heating in the dermis is rapid and specific. Geometric considerations include size and shape of the coil so as to minimize distance between the coil and the skin target. Rapid and specific heating of the dermis, as is achieved using an intense alternating magnetic field, minimizes the total heat volume that collateral tissues are subject to.

Variations in cooling of the skin surface may be achieved by increasing the volume of coolant to the device, or surface of the skin. These variations may be optimized to provide additional protection of the tissue proximal to the device from the effects of heating.

Disposition of a heat sink between the coil and tissue may provide dispersion and distribution of excess heat. As the treatment progresses, heat may build up inside the tissue and at the interface of the device, thereby heating the device tip. The presence of a thermally conductive mass between the surface of the tissue and the device tip serves to minimize heating of the device, and may additionally serve to maintain an ambient temperature at the tissue surface.

In certain instances, coil geometry may result in uneven heating at the tip of the device. For example, eddy currents may form in the skin that reflect the shape of the coil, particularly where the coil is a toroid, a ring-shaped heating pattern may result in the tissue. The removal of heat in this instance serves to minimize the build-up of excess heat, i.e. the heat is distributed more evenly at the skin surface.

A scaffold or lattice structure may be placed within tissues to provide support. The structure may be fixed or fused in place using methods described herein. For example, localizing a scaffold made of polylactic acid, or a similar polymer in proximity to fat layers found in or under skin could prove beneficial in the treatment of cellulite fat. Cellulite produces an unattractive profile on the surface of skin due to the fat being squeezed between tissue structures resulting in upwelling of "fingers" of fat, which then distend the skin surface. Cellulite's cause is unclear, although it may result from fatty distension of the superficial fascia, which connects the dermis to the deep fascia. Attachment points to the dermis may be patent while surrounding areas lose structure and bulge, producing the "cobblestone" appearance on the surface of the skin. By increasing the number of attachment points, or by fixing a mesh-like substrate in place to minimize bulge, or by heating the fat to achieve melting and flowing into the scaffold, cosmesis may conceivably be improved. The devices and methods described herein may be used to heat and melt fat layers.

Another embodiment of the present invention allows for treatment of acne, hair removal or treatment of varicose veins. It has been determined that the production of a critical amount of heat in tissue can lead to a cascade of events that results in a therapeutic effect. Acne can be treated by causing thermal damage in the affected skin, and hair removal can result from thermal damage to the hair follicles. The exact biologic mechanism behind these treatments is unclear, but tissue tightening may play a role. Alternatively, sub-lethal damage to the hair follicles can actually result in stimulating hair growth. Sub-lethal damage leads to a cascade of wound-response events such as the production of cytokines, interleukins and heat-shock proteins. These endogenous events can be beneficial and probably underlie the salient events in, for example, stimulating hair-growth. The instant invention can induce all of these events.

Treatment of skin wrinkles sometimes can employ botulism toxin, whereupon an injection of toxin in or around the nerves associated with the wrinkle temporarily relax the muscle leading to reduction in the appearance of the wrinkle. Recently, electrosurgical ablation of the nerve has been shown to result in a good cosmetic effect and may benefit from being permanent. The problem with electrosurgical ablation of the nerves is the same as the problems associated with electrosurgical generators in other procedures, i.e. there is a risk of burning and excess heating. The present invention provides a means with which to ablate the nerve in a non-contact mode, whereby a metal tip catheter may be placed into the nerve, or near the nerve, and the tip exposed to a magnetic field generated from a coil in the near vicinity.

Coagulation is a very important technique in surgery as it provides a means to kill tissue without dissection, thus eliminating potentially toxic smoke and char, and by not removing tissue, allowing for mechanical integrity to be maintained for a period of time. Standard electrosurgical and electrocautery devices usually produce smoke when used to coagulate tissue (smoke is a potential source of carcinogens or viruses), and dry tissue tends to stick to the electrosurgical electrode which then results in re-bleeding when the electrode is removed from the treatment site. A non-contact way of coagulating tissue, using the instant invention, would be or paramount importance in surgery. The instant invention exhibits the benefit and when the tissue is heated and dessicates, coupling between the magnetic field and tissue decreases thus limiting the heating and eliminating the possibility of smoke or charring.

The following examples are given for the purpose of illustrating various embodiments of the invention and are not meant to limit the present invention in any fashion.

EXAMPLE 1

Applicator

Figure 5:
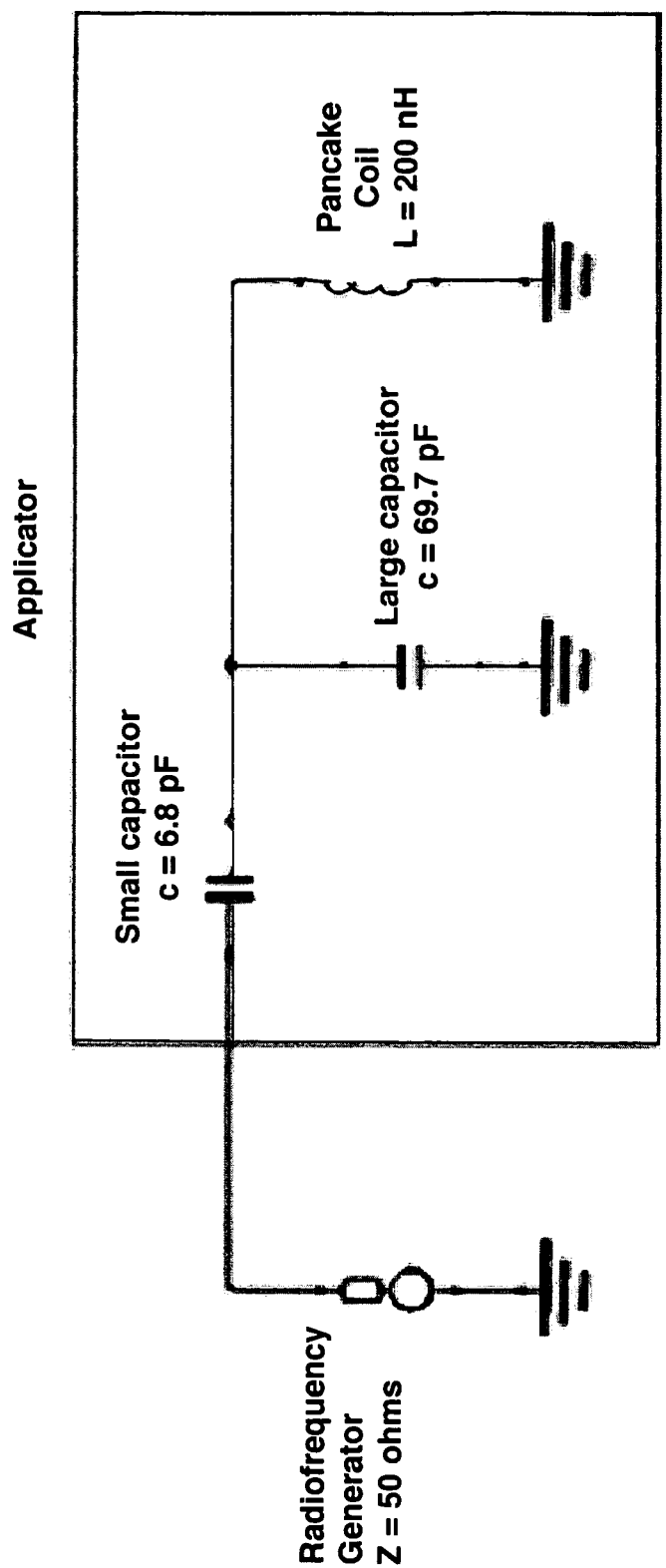
FIG. 5 depicts a circuit diagram of the applicator.

The pancake coil is made from 3.5 turns of 0.125" OD copper refrigeration tubing and has a diameter of 1.4". The coil must be hollow tubing to allow water or other cooling fluid to flow through it and dissipate the ~500 W of heat generated. The main capacitor (FIG. 1, 2260) has a value of ~70 pF which resonates with the coil at 40.68 MHz (FIG. 5). Earlier prototypes were made with a Teflon dielectric (Kr=2.2), but the size of the capacitor became too unwieldy to use in a handheld device. Capacitance can be calculated using the formula for a cylindrical capacitor: $C=(2\pi * Kr * \mu o)/(\ln(b/a))$, where, C=capacitance in pF per unit length, Kr=dielectric constant (9.8), µo=permittivity of free space=8.85 pF/m, b=outer diameter, a=inner diameter The length of the capacitor is inversely proportional to the Kr of the dielectric used, so alumina was chosen for its high Kr and its other desirable properties: Good thermal conductivity—30 W/m*K; High dielectric strength—220 ACV/mil; High dielectric constant—9.8; Available in tube form at low cost; Dimensions compatible with available copper pipe sizes. The particular alumina tube used is 3.5" long, 0.625" OD, 0.500" ID, 99.8% alumina (CoorsTek part #65677). The inner and outer "plates" of the cylindrical capacitor are copper pipes that fit closely to the inner and outer diameters of the alumina tube.

It is critical that the copper tubes fit the alumina as closely as possible, as any air gaps will act as low value series capacitors and offset the advantage of the high Kr material. Since it is impossible to completely eliminate the air gaps, the entire capacitor assembly is potted in silicone with a Kr of 2.7 to regain some of the capacitance lost by the gaps, and also to help prevent the high voltage RF arcs which are bound to occur at these high voltages. The silicone, through vacuum encapsulation, completely surrounds all high voltage points on the device. The tuning capacitor (FIG. 1, 2330), is formed in the same way as the main capacitor, although much smaller in value and size.

Shielding was found to be an important part of the design to reduce circuit detuning caused by the operator's hand, as well as reduce stray radiation from the connecting coax and RF generator. The shield encloses all the internal workings of the device, and is made from 1" copper pipe and an end cap. The shield also serves as a liquid tight container to hold the silicone (Momentive RTV615) during the vacuum encapsulation process.

Water-cooling is used to effectively cool both the coil and the coaxial capacitor assembly. Water flows in series through the center capacitor pipe, then the coil, and back through the copper tubing soldered to the outer capacitor pipe. At a power level of 500 W and 0.75 liters/min flow, the water temperature rise is about 9° C.

A resonant circuit was the topology chosen to maximize the current in the coil because this type of circuit has the property that the circulating current is approximately Q times the applied current, and the Q of this circuit is about 60. The primary goals of the circuit are to maximize the current in the coil as well as provide a good impedance match to the 50 ohm RF generator driving it.

The alumina tube is cut to length using a wet cutting diamond saw. The inner pipe is then prepared by turning it down on a lathe to a size that just slides into the ceramic without forcing it. Copper disks and short lengths of 0.125" copper tubing are soldered into the ends of the pipe, one going to the flexible silicone water tubing, and the other to the pancake coil.

A small batch of RTV615 is mixed up and de-aired in a vacuum chamber using a Welch 1400 vacuum pump. The mixture is considered de-aired after it foams up and then recedes (~30 minutes). About 1 ml of the RTV is poured into one end of the vertically held inner pipe/ceramic assembly and cured at 100° C. for one hour, forming a silicone "plug" in that end to prevent the liquid RN from running out during the next step. After cooling, the assembly is inverted and more RTV is poured into the other end and allowed to sink in and fill the gaps between the inner pipe and ceramic under vacuum. After sufficient time in the vacuum (no more rising air bubbles visible), the assembly is removed from the vacuum and again cured at 100° C. for one hour.

Adhesive backed copper foil tape is tightly wrapped on the outer diameter of the ceramic assembly over a distance slightly shorter than the outer capacitor pipe. The purpose of the tape is to get a tight fitting conductor around the ceramic with minimal air gaps. The tape is mechanically weak and not thick enough to adequately conduct the heat generated, so copper pipe couplers are then bored out to slide over the layer of copper tape, and will be soldered in place once the initial tuning is completed. The "ring" pipe is bored out to tightly fit the ceramic at this time as well. About 0.4" of free ceramic is left on the end for high voltage insulation and spacing.

Next, the pancake coil is wound from the 0.125" refrigeration tubing, and the short end of the tubing from the center is coupled and soldered to the tubing stub on the capacitor assembly. The other (long/grounded) end of the tubing is positioned parallel and against the outer pipe (ground), and is temporarily held in place with copper tape for tuning.

A length of test coax from a network analyzer is temporarily soldered between ground and the ring. The outer pipe and ring are slid back and forth to obtain an impedance match at a frequency higher than the final operating frequency, knowing that the frequency will drop after encapsulation with silicone. Once the correct position is found, the grounded tubing of the pancake coil is soldered along the outer pipe and the gap between the copper foil and outer pipe is flooded with solder.

The silicone water tubing is now attached to the other stub of 0.125" tube on the inner pipe with a bus wire "hose clamp" and the connection covered with heatshrink. The Teflon sleeve is then slipped over this connection for high voltage insulation.

At this point the 1" copper shield pipe is positioned over the inner workings, with the grounded end of the coil's copper tubing exiting the shield through a slot in the side. The flexible silicone water hose and coax cable are fed through holes in the pipe cap; the coax braid is soldered to the inner wall of the shield, and the coax center conductor to the ring on the ceramic assembly. After pressing the pipe cap in place, and centering the ceramic assembly in the shield, the ground tubing is soldered to the shield and the slot filled with solder for a liquid tight seal. A final tuning check is made with a network analyzer with the shield in position, and any necessary pre-encapsulation adjustments are made.

Next, another (~80 g) batch of RTV is prepared and de-aired in the vacuum chamber as before. With the device held vertically and open at the top, the assembly is slowly filled with RN and then vacuum pumped for about an hour to remove all air bubbles. The vacuum process is complete when air bubbles stop rising to the surface. The device is then removed from the vacuum and cured for 4 hours at 65° C. The longer, lower temperature curing cycle is used because it is below the coax cable's maximum temperature rating. After curing and cooling, the second silicone water hose is attached to the copper ground tubing with a bus wire "hose clamp" and the connection covered with heat shrink.

EXAMPLE 2

Tissue Tightening In Vitro

Ovine and human tissue samples were cut into 2 cm×2 cm sections and inductively treated using 400 W power generated from a an ENI 6B power supply operating at 13.6 MHz. The coil was 2 cm in diameter and placed 2 mm from the tissue. Exposure was for 20-30 seconds. Samples of lung, artery, and skin demonstrated macroscopic shrinkage of approximately 5-20% depending on length of exposure. Skin and lung samples were placed in formalin and evaluated by thin section histology. Examination of Masontrichome stained sections demonstrated that collagen fibrils were packed more closely together in the treated versus untreated sections.

Figure 6:
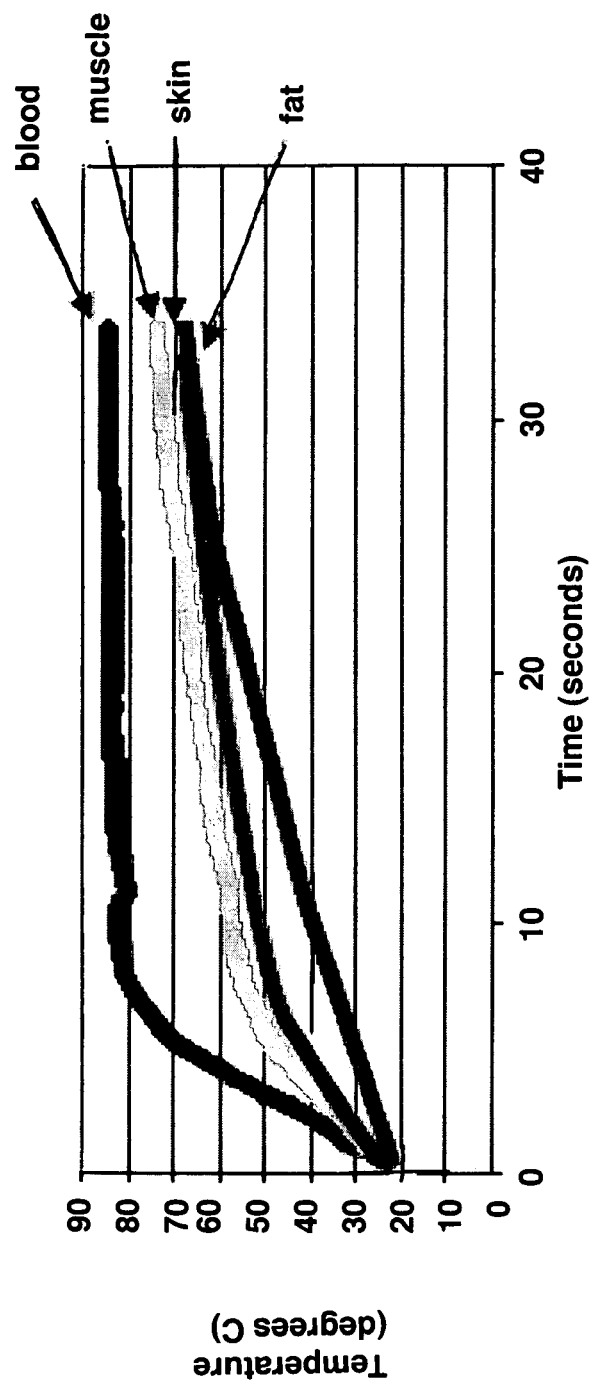
FIG. 6 shows measurements taken at 27 MHz and 600 W. Bovine muscle, bovine fat, ovine skin, and human blood were used for comparison. The tissues were cut to 2×2×5 cm samples. Each sample was placed directly on the cap of the 27 MHz device and imaged from above with a Raytek IR thermometer. The device was activated and the time to heat was recorded. (n=3 for each tissue type).

FIG. 6 shows measurements taken at 27 MHz and 600 W. Bovine muscle, bovine fat, ovine skin, and human blood were used for comparison. The tissues were cut to 2×2~5 cm samples. Each sample was placed directly on the cap of the 27 MHz device and imaged from above with a Raytek IR thermometer. The device was activated and the time to heat was recorded, (n=3 for each tissue type).

Figure 7:
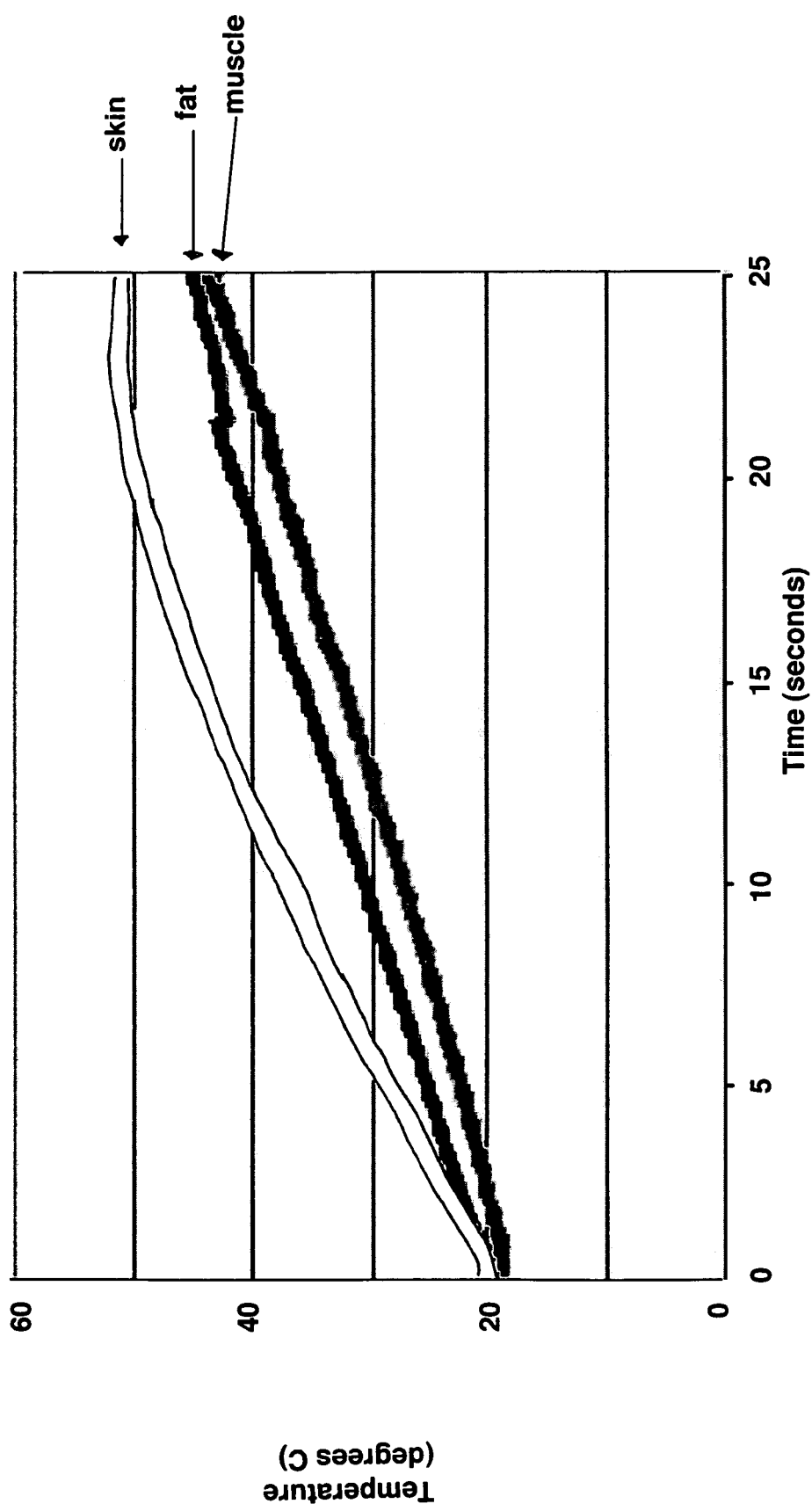
FIG. 7 shows porcine fat, muscle and skin were used for comparison. The tissue samples were measured for thickness to ensure consistency between samples. The samples were between 1.5-2.0 mm in thickness. The samples were placed on the faceplate which is 4 mm thick PVC and imaged from above with a Raytek IR thermometer. The device was turned on and the time for the sample to reach 70° C. was recorded. The IR thermometer is limited to recording the tissue surface opposite that which is in contact with the device. Therefore, it is believe that the actual temperature of the tissue was greater than indicated on the graph.

FIG. 7 shows porcine fat, muscle and skin were used for comparison. The tissue samples were measured for thickness to ensure consistency between samples. The samples were between 1.5-2.0 mm in thickness. The samples were placed on the faceplate which is 4 mm thick PVC and imaged from above with a Raytek IR thermometer. The device was turned on and the time for the sample to reach 70° C. was recorded. The IR thermometer is limited to recording the tissue surface opposite that which is in contact with the device. Therefore, it is believe that the actual temperature of the tissue was greater than indicated on the graph.

EXAMPLE 3

Tissue Tightening and Dermal Thickening In Vivo

Rat skin was treated with the coil device at 40 MHz and 350 W power delivery. The device was held juxtaposed to the skin of anesthetized rats until visible shrinkage was evident without cooling (treatment time tt=24 seconds), with cooling (that is, with the refrigerant circulating through the coil and endplate, tt=29 seconds) and at tt=27 seconds. A grid was drawn on the back of the animal prior to treatment and was photographed before and after treatment and on post op day one. The image was digitized and the grids were compared down to the pixel for acute shrinkage. The treatment site was biopsied on post op day two for acute wound response and on post-treatment day 21 to ascertain collagen deposition. Temperature of the epidermis was also measured following treatment. After treatment, the temperature of the surface of the skin was at or around 42° C.

By measuring the distance between the gridlines on the skin, it was possible to determine that acute shrinkage of 5% with cooling and 8.5% without cooling occurred. After 1 day, the skin exhibited a sustained shrinkage of 2.5% with cooling and an increase to 15.9% without cooling. Consistent results were obtained with guinea pig skin, which is known to better mimic human dermal tissue. Treated guinea pig skin shrunk 10.9% with cooling and 11.6% without cooling immediately following treatment.

EXAMPLE 4

Tissue tightening and dermal thickening using 27.2 MHz

The dorsa of four Sprague-Dawley rats were shaved, then the skin was inductively treated using 600 W power generated from a 27.2 MHz power supply. The two-turn pancake coil was 1.5 cm in diameter, and placed against the tissue using a 2 mm spacer composed of Teflon. Exposure was from 5 to 10 seconds and cooling of the coil was used. Contraction of the tissue was noted after several seconds of treatment. Biopsies were taken at 21 or 28 days, and histologically stained using eosin or Mason Trichome.

Figure 8A:
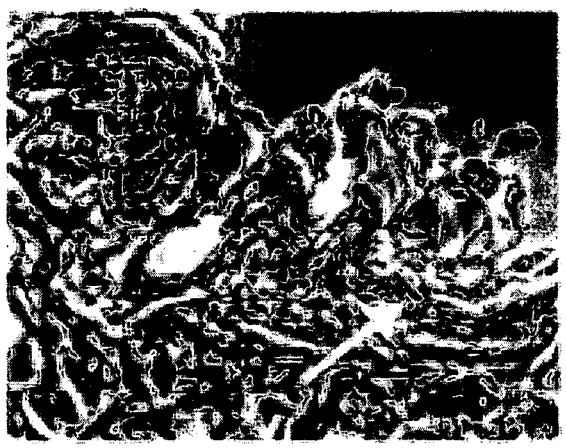
FIGS. 8A-8C show biopsied samples at the two-week post-treatment time point (FIGS. 8B-8C) demonstrating a thickening of the dermis as compared to untreated controls (FIG. 8A).
Figure 8B:
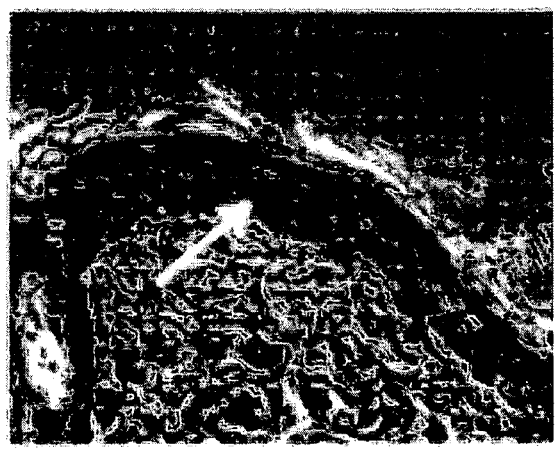
Figure 8C:
Figure 9A:
FIGS. 9A-9B show biopsied samples before and after treatment demonstrating a production of neo-collagen in treated tissues (FIG. 9B) as compared to the untreated controls (FIG. 9A).
Figure 9B:
Figure 10:
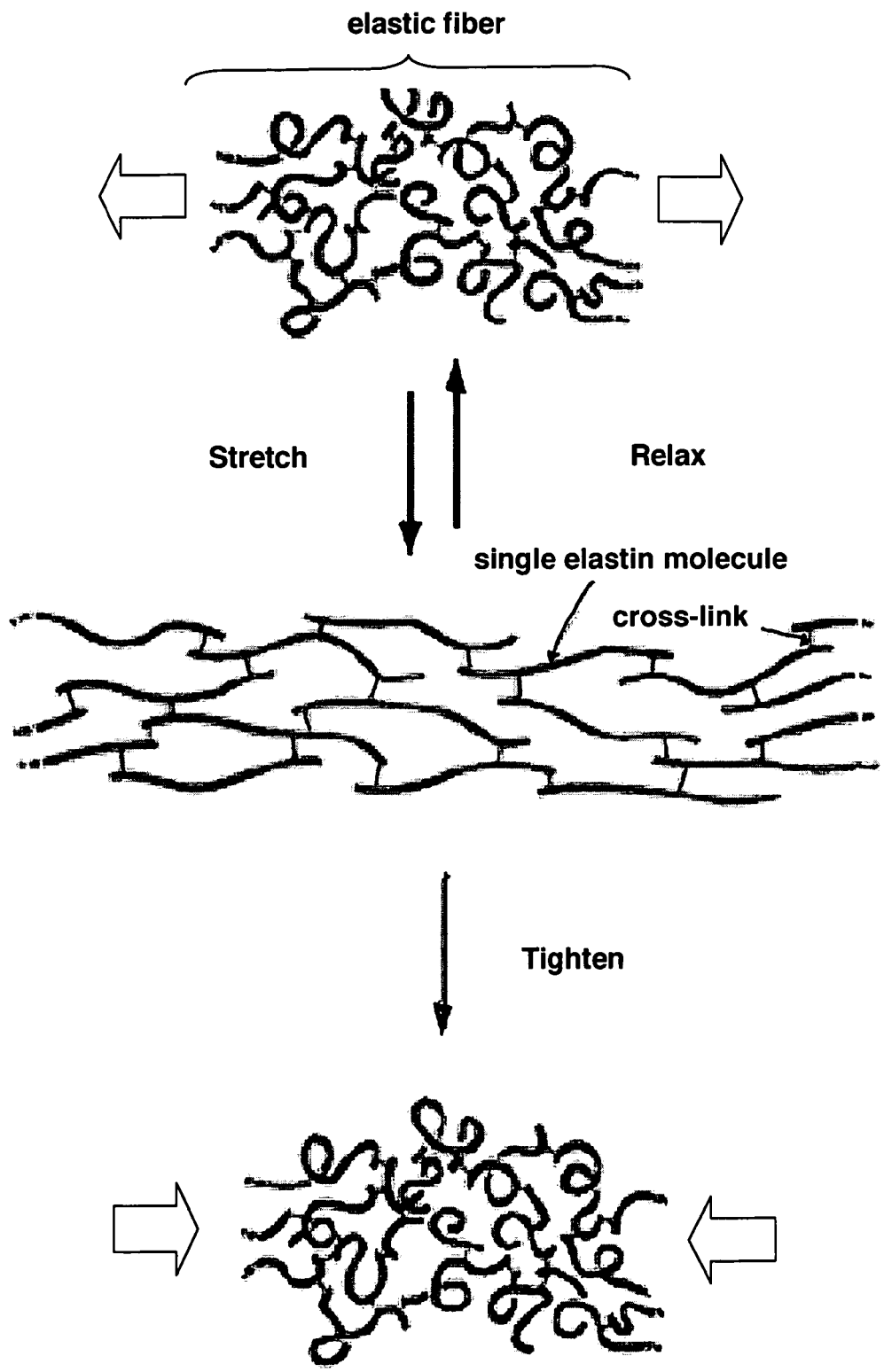
FIG. 10 shows a model of the expected mode of action produced by inductive heating on collagen within the treated tissues.

Biopsied samples at each timepoint showed a thickening of the dermis as compared to untreated controls (FIGS. 8A-8C), as well as production of neo-collagen (FIGS. 9A-9B). FIG. 10 shows a model of the expected mode of action produced by this inductive heating using alternating magnetic field energy on the collagen within the treated tissues; the collagen denatures and coagulates, sometimes involving cross-linking between the proteins, resulting in a shrinkage in the volume of the tissue.

EXAMPLE 5

Skin Tightening in Human Subjects

A 27.1 MHz radiofrequency generator (Comdel CV 500) was fitted with a hand piece comprised of a 3 cm diameter, multi-turn coil and matching network. Four human subjects received treatments of from 8 to 11 seconds on the abdomen at 250 W power output from the Comdel. Skin tightening was apparent after 72 days as evidenced by a reduction in visible wrinkles, skin smoothing and reduction of waist size. The visual appearance of the skin (skin rejuvenation) was also improved.

The following references are cited herein.
1. U.S. Pat. No. 7,189,230.
2. Leitgeb, N. Bioelectomagnetics 2010, 31:12-19.
3. Franco, W. et al, Lasers Surg. Med. 2010; 42:361-370.
4. U.S. Pat. No. 7,463,251
5. Anderson, R R, Arch Dermatol, 2003, 139:787-788.
6. Gilchrest et al., Plast. Reconstr. Surg. 1982; 69:278-83.
7. Klein, M. 2008 Deep Heat, www.emedicine.medscape.com.
8. Cameron, M. In: Physical Agents in Rehabilitation, Saunders.

Any patents or publications mentioned in this specification are indicative of the levels of those skilled in the art to which the invention pertains. These patents and publications are herein incorporated by reference to the same extent as if each individual publication was specifically and individually incorporated by reference. One skilled in the art will readily appreciate that the present invention is well adapted to carry out the objects and obtain the ends and advantages mentioned, as well as those inherent therein. It will be apparent to those skilled in the art that various modifications and variations can be made in practicing the present invention without departing from the spirit or scope of the invention. Changes therein and other uses will occur to those skilled in the art which are encompassed within the spirit of the invention as defined by the scope of the claims.

What is claimed is:

1. A device for treating skin, the device comprising:
a copper tube comprising:
- a straight central portion for conducting radiofrequency energy;
- a distal coil configured to generate a high frequency alternating magnetic field from the radiofrequency energy; and
- a proximal exit pipe;

an inner cylinder surrounding at least part of the straight central portion of the copper tube;
an outer cylinder surrounding at least part of the copper tube and the inner cylinder; and
a hand piece, comprising:
- a main housing disposed over the outer cylinder; and
- a shield disposed over the distal coil of the copper tube and configured to contact the skin.

2. The device of claim 1, further comprising:
a ceramic insulator surrounding at least part of the inner cylinder; and
two capacitor rings disposed at separated locations over the ceramic insulator,
wherein the proximal exit pipe portion of the copper tube is in electrical contact with the two capacitor rings, and
wherein the outer cylinder surrounds at least part of the ceramic insulator and the two capacitor rings.

3. The device of claim 2, wherein at least one of the two capacitor rings is movable along the ceramic insulator to adjust a spacing between the two capacitor rings and thereby adjust an impedance match between a source of radiofrequency energy supplying the device and the distal coil.

4. The device of claim 1, further comprising a source of radiofrequency energy removably coupled with the straight central portion of the copper tube.

5. The device of claim 1, wherein the distal coil of the copper tube comprises an induction coil.

6. The device of claim 1, wherein the inner cylinder comprises polytetrafluoroethylene (PTFE).

7. The device of claim 1, wherein the copper tube is configured to conduct a coolant through the distal coil to cool the skin during a skin treatment, and wherein the coolant exits the copper tube via an opening at a proximal end of the proximal exit pipe.

8. The device of claim 1, further comprising
a cooling system coupled with the hand piece, the cooling system comprising:
a coolant housing; and
a pipe having an exit nozzle at or near the shield of the hand piece.

9. The device of claim 1, further comprising a feedback mechanism configured to control treatment of the skin.

10. The device of claim 9, wherein the feedback mechanism is selected from the group consisting of a heat sensor, a thermocouple, a thermistor, an infrared thermometer, an ultrasound transducer, and a tissue impedance measurement device.

11. The device of claim 1, further comprising an endplate inside the shield and coupled with the distal coil.

12. The device of claim 11, further comprising a conductive shield disposed between the endplate and the shield of the hand piece to reduce capacitive coupling of the distal coil with the skin.

13. The device of claim 1, wherein the shield of the hand piece is removable from the main housing and is disposable.

* * * * *